United States Patent [19]

Simon

[11] Patent Number: 5,928,657
[45] Date of Patent: *Jul. 27, 1999

[54] CLEANING COMPOSITION IN THE FORM OF A RINSABLE TRANSPARENT GEL

[75] Inventor: Pascal Simon, Vitry sur Seine, France

[73] Assignee: L'Oreal, Paris, France

[ * ] Notice: This patent is subject to a terminal disclaimer.

[21] Appl. No.: 08/962,447

[22] Filed: Oct. 31, 1997

[30] Foreign Application Priority Data

Nov. 4, 1996 [FR] France .................................. 96 13406

[51] Int. Cl.$^6$ .............................. A61K 7/00; A61K 7/06; A01N 43/04; C07H 1/00
[52] U.S. Cl. .......................... 424/401; 424/70.1; 514/23; 514/941; 514/944; 536/1.11; 536/18.3
[58] Field of Search .................................. 424/401, 70.1; 514/23, 941, 944; 536/1.11, 18.3

[56] References Cited

U.S. PATENT DOCUMENTS

| | | | |
|---|---|---|---|
| 4,268,498 | 5/1981 | Gedeon et al. ............................ | 424/59 |
| 4,482,537 | 11/1984 | El-Menshawy et al. ................. | 424/59 |
| 4,687,843 | 8/1987 | Smolin et al. .......................... | 536/18.3 |
| 5,607,980 | 3/1997 | McAtee et al. .......................... | 514/476 |
| 5,641,479 | 6/1997 | Linares et al. ........................ | 424/70.21 |

FOREIGN PATENT DOCUMENTS

| | | |
|---|---|---|
| 0 274 812 | 7/1988 | European Pat. Off. . |
| 0 588 379 | 3/1994 | European Pat. Off. . |
| 2 237 615 | 2/1975 | France . |
| 41 39 935 | 6/1993 | Germany . |
| WO 92/07543 | 5/1992 | WIPO . |
| WO 93/08840 | 5/1993 | WIPO . |
| WO 94/17830 | 8/1994 | WIPO . |

OTHER PUBLICATIONS

Chemical abstracts, vol. 93, No. 18, Nov. 3, 1980, pp. 344–345.

*Primary Examiner*—Shelley A. Dodson
*Assistant Examiner*—Marina Lamm
*Attorney, Agent, or Firm*—Oblon, Spivak, McClelland, Maier & Neustadt, P.C.

[57] ABSTRACT

A cosmetic composition consisting essentially of (i) a fatty phase, (ii) at least one fatty acid ester of a $C_5$–$C_7$ carbohydrate, and (iii) at least one polyol.

20 Claims, 3 Drawing Sheets

CLEANING COMPOSITION IN THE FORM OF A RINSABLE TRANSPARENT GEL

BACKGROUND OF THE INVENTION

1. Field of the Invention

The invention relates to compositions for cleaning the skin which preferably are transparent, water-rinsable, gelled in appearance, and rich in oils.

2. Discussion of the Background

Cleaning the skin is very important, especially for face care. It must be as effective as possible because the fatty residues such as excess sebum, residues of the cosmetic products which are employed daily, and make-up products, especially the water-resistant "waterproof" products, accumulate in skin folds and at the surface of the skin and can block skin pores and entail the appearance of spots. Poor cleaning, and in particular poor rinsing, are often responsible, among other causative factors, for a sallow complexion.

In the field of skin cleaning the removal of make-up of water-resistant "waterproof" types, of transfer-free products and of heavy make-ups, like stage make-ups, requires the use of oily compounds to be effective. Oily compositions are recognized for their effectiveness as cleaning agents and/or make-up removers. They in fact allow lipophilic soiling and make-up to be dissolved very easily, in particular the "waterproof" and transfer-free make-ups which are known to be difficult to remove.

However, the use of an oily composition is not always free from disadvantages:

oily lotions run and are difficult to handle,
oily compositions, usually thickened with waxes, silicas, modified clays or polyvalent salts of fatty acids, are usually turbid or opaque and relatively unattractive in appearance; their stability over time is often limited,
oily compositions on the whole are difficult to remove:
either they are removed mechanically with the aid of a swab, which frequently results in a skin irritation; moreover, this type of application has the disadvantage of leaving an oily film on the skin;
or surfactants are incorporated in them to make them water-rinsable and tolerance for them is lost, in particular in the case of sensitive skins; in addition, some surfactants (especially oxyethylenated sorbitan esters) are easily oxidizable and the rinsability of these compositions is not the best.

Oily compositions for cleaning the skin, in the form of a stable transparent gel including a hydrophilic sucrose fatty ester and a polyol are known, for example from U.S. Pat. No. 4,379,755, JP-5-229916 and JP-60-115509. However these compositions have an insufficient rinsability. Moreover, sucrose derivatives exhibit a high instability to temperature.

Objects of the Invention

One object of the invention is to improve the rinsability of transparent oily gels including polyols.

BRIEF DESCRIPTION OF THE DRAWINGS

FIGS. I, II and III each show the development of turbidity of two aqueous solutions on which 0.5 ml of rinsable gel are deposited (Compositions 1a and 2a, 1b and 2b, 1c, 2c and 3c, respectively).

DETAILED DESCRIPTION OF THE INVENTION

Figure 1:
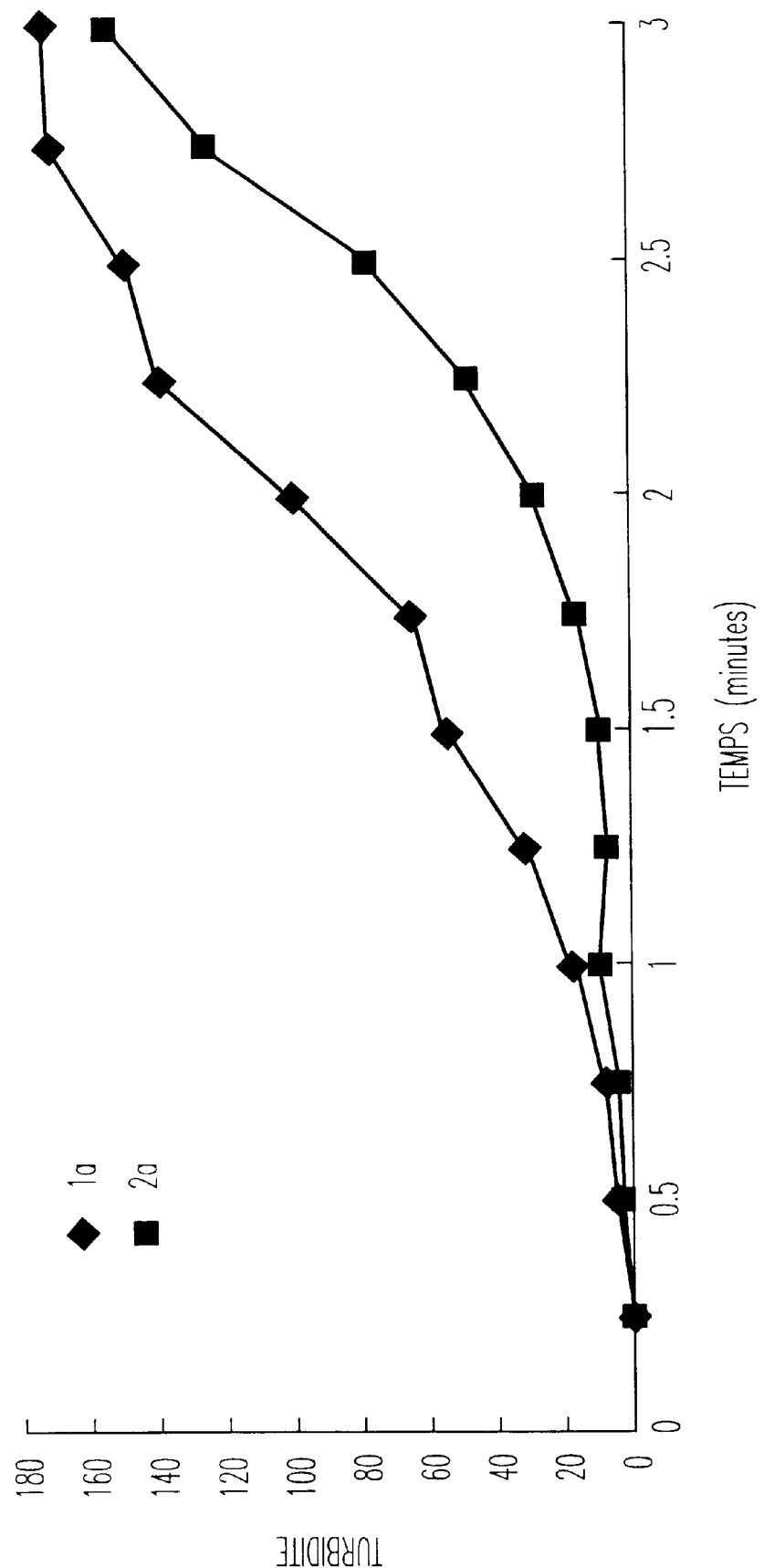
Figure 2:
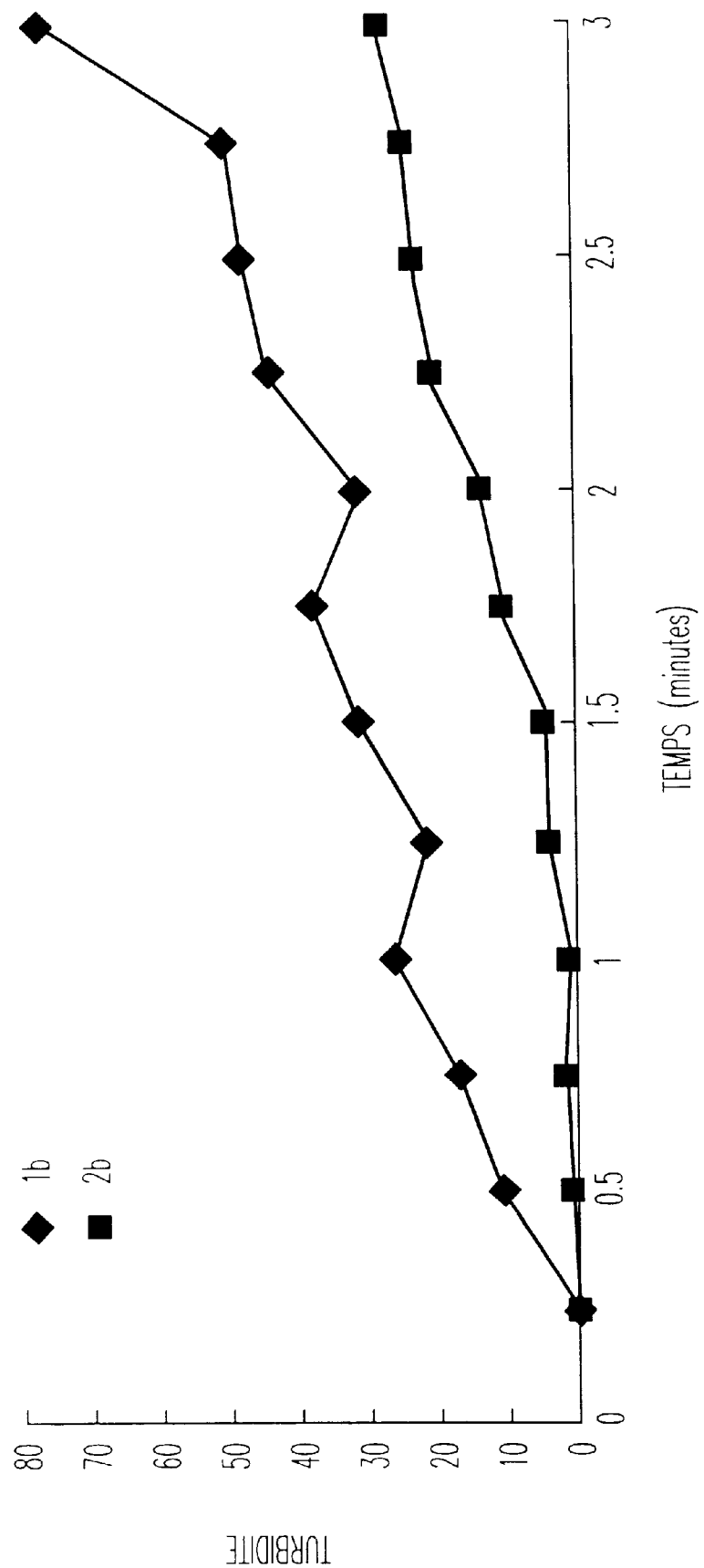
Figure 3:
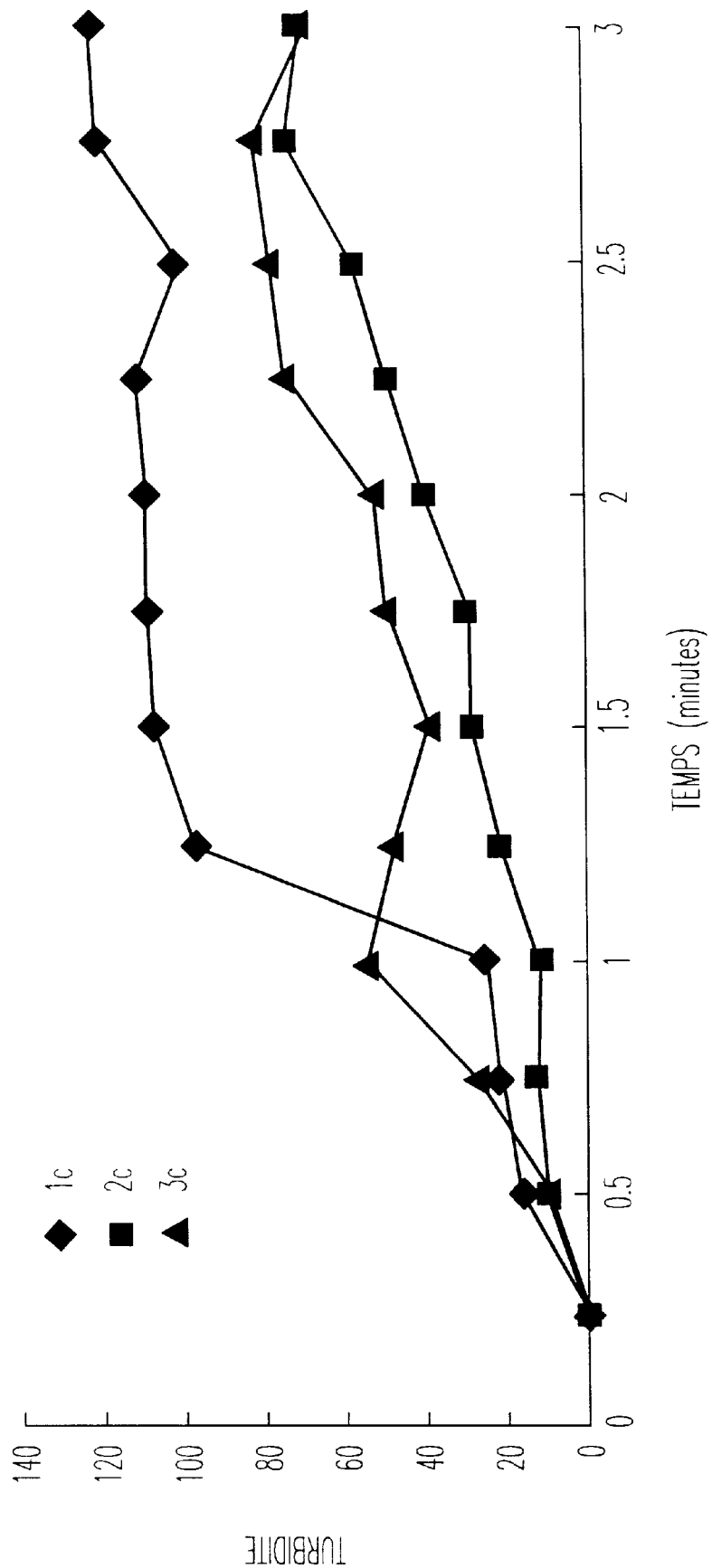

The subject-matter of the invention is compositions for cleaning the skin which have the appearance of, or include, a stable transparent gel exhibiting an improved rinsability. These compositions comprise, consist essentially of, or consist of:

(i) a fatty phase,
(ii) at least one $C_5$–$C_7$ carbohydrate fatty ester, and
(iii) at least one polyol.

The word "transparent" means that through a transparent bottle containing the composition it is possible to distinguish the characters printed on a newspaper page placed behind this bottle. Preferably, the transparent bottle is 6–12 cm thick.

The viscosity of the compositions according to the invention is preferably higher than 2 Pa s, more preferably higher than 4 Pa s and still more preferably higher than 5 Pa s including 6, 7, 8, 9, 10, 15, 18, 20, 25, etc. Pa s. It is preferably lower than 25 Pa s. This viscosity is determined at room temperature (20–25° C.) and room pressure, with a RHEOMAT 180 (METTLER) at 200 rpm.

The compositions of the invention also preferably include water. In this case they are advantageously in the form of an oil-in-water emulsion which has the appearance of a gel.

$C_5$–$C_7$ carbohydrates as used herein is intended to mean pentoses, hexoses and heptoses (not reduced) and their alkyl holoside derivatives in which the alkyl group contains from 1 to 6 carbon atoms. The carbohydrates are advantageously chosen from those which have a chain containing 6 carbon atoms and they are preferably chosen from glucose, fructose and their $C_1$–$C_6$ alkyl glucoside and alkyl fructoside derivatives. Still more preferably the carbohydrate is glucose or an alkyl glucoside derivative like, for example, 1-methyl glucoside.

$C_5$–$C_7$ carbohydrate fatty esters as used herein is intended to mean the compounds obtained by reaction of a fatty acid containing a saturated or unsaturated chain containing from 8 to 30 carbon atoms, preferably from 12 to 22 carbon atoms, and still more preferably from 16 to 20 carbon atoms, with a carbohydrate chosen from pentoses, hexoses, heptoses and their alkyl holoside derivatives in which the alkyl group contains from 1 to 6 carbon atoms.

The $C_5$–$C_7$ carbohydrate fatty ester may contain a mixture of mono-, di-, tri- and tetraester derivatives.

The $C_5$–$C_7$ carbohydrate fatty esters are advantageously oxyalkylenated. The $C_5$–$C_7$ carbohydrate fatty esters are preferably etherified by one or more oxyethylene or oxypropylene fragments, the total of the oxyethylene or oxypropylene substituents representing in all from 5 to 200 and preferably 15 to 150 alkylene oxide units.

All the hydroxyl functional groups of the carbohydrate derivative, employed in the compositions according to the invention may advantageously substituted by an ester group or by an alkylene oxide group.

Such compounds are well known to a person skilled in the art. A number of these compounds are available commercially. It is possible, for example, to err ploy the derivatives sold under the trade name Glucamate® by Amerchol.

The $C_6$ carbohydrate fatty esters are chosen advantageously from compounds corresponding to the formula (I):

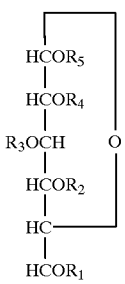
(I)

in which
$R_1$ is a group of formula (III):

(III)

R' being chosen from $C_8$–$C_{30}$ and preferably $C_{12}$–$C_{22}$ saturated or unsaturated, linear or branched alkyl groups, $R_2$, $R_3$ and $R_4$, which are identical or different, denote a group chosen from:

a hydrogen atom, a group of formula (II):

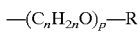
(II)

with n=2 or 3; p is an integer ranging from 2 to 50; R denotes a hydrogen atom or a $C_1$–$C_6$ alkyl group, a group of formula (III):

(III)

R' being chosen from $C_8$–$C_{30}$ and preferably $C_{12}$–$C_{22}$ saturated or unsaturated, linear or branched alkyl groups, at least one of $R_2$, $R_3$ and $R_4$ being a group of formula (II), the total of the oxyalkylene residues, $\Sigma p$, being between 5 and 200, $R_5$ being a saturated or unsaturated, linear or branched $C_1$–$C_6$ alkyl group.

The choice is preferably:

$R_5$=$CH_3$, at least two groups from $R_2$, $R_3$ and $R_4$ correspond to the formula (II), $\Sigma p$ is between 15 and 150,

R=H,

R' is chosen from $C_{16}$–$C_{20}$ alkyl groups, none of the groups $R_2$, $R_3$ and $R_4$ is a hydrogen atom.

The compositions according to the invention preferably include, by weight relative to the total weight of the composition, from 0.5 to 50% of one or a mixture of invention $C_5$–$C_7$ carbohydrate fatty ester(s), more preferably from 2 to 20% including 5, 10 and 15%.

The compositions according to the invention also include at least one polyol. This polyol may optionally be oxyalkylenated. The polyol advantageously includes at least two free hydroxyl functional groups. This polyol may be chosen from ethylene glycol, propylene glycol, 1,3-butylene glycol, dipropylene glycol, glycerine, polyglycerines like diglycerine, triglycerine and tetraglycerine, glucose, maltose, maltitol, sucrose, fructose, sorbitol, sugars originating from the decomposition of starch and mixtures thereof.

The polyol represents preferably from 0.5 to 60% by weight relative to the total weight of the composition, more preferably from 2 to 40% and still more preferably from 5 to 30% including 10, 15, 20 and 25%.

The nature of the fatty phase forming part of the composition of the emulsions according to the invention is not critical; it may thus comprise any of the compounds that are already generally known as suitable for the manufacture of emulsions of oil-in-water type. In particular, these compounds may be chosen, alone or as mixtures, from the various fatty substances, oils of vegetable, animal or mineral origin, natural or synthetic waxes and the like.

Oils that can be employed in the present invention include oils of vegetable or animal origin like, for example, squalane, copra oil, macadamia oil, mink oil, turtle oil, soya oil, grape seed oil, sesame oil, corn oil, rapeseed oil, sunflower oil, cotton oil, avocado oil, olive oil, castor oil, jojoba oil and groundnut oil; hydrocarbon oils such as paraffin oils, petrolatum, isododecane, isohexadecane, isoparaffins; silicone oils like polydimethylsiloxanes, cyclopolydimethylsiloxanes, polymethylphenylsiloxanes, polysiloxanes modified with fatty acids, polysiloxanes modified with fatty alcohols, polysiloxanes modified with polyoxyalkylenes and fluoro silicones; perfluoro and/or organofluoro oils; higher fatty acids such as myristic acid, palmitic acid, stearic acid, behenic acid, oleic acid, linoleic acid, linolenic acid, isostearic acid, higher fatty alcohols such as cetanol, stearyl alcohol and oleyl alcohol; mono- and diesters among which there may be mentioned in particular isopropyl myristate, isopropyl palmitate, butyl stearate, hexyl laurate, isononyl isononanoate, 2-ethyl-hexyl palmitate, 2-hexyldecyl laurate, 2-octyldecyl palmitate, 2-octyldodecyl myristate, di-2-ethylhexyl succinate, diisostearyl malate, 2-octyldodecyl lactate, glycerine triisostearate, di-n-butyl adipate, di(2-ethylhexyl) adipate, ethylene glycol dioleate, ethylene glycol diisotridecanoate, ethylene glycol diisostearate and neopentyl glycol dicaprylate.

An oil or a mixture of oils which has a refractive index $^{20}n_D \leq 1.45$ is preferably employed.

The fatty phase may represent from 1 to 95% by weight of the total weight of the composition, preferably from 20 to 85% and still more preferably from 40 to 80% including 50, 60 and 70%.

Water represents preferably from 0.01 to 30% by weight relative to the total weight of the composition. Water represents advantageously from 2 to 20% by weight relative to the total weight of the composition, including 5, 10 and 15%.

Water is usually intended to mean pure water. However, some or all of the water employed in the compositions according to the invention may optionally be chosen from among mineral or thermal waters. In general a mineral water is suitable for consumption, which is not always the case with a thermal water. Each of these waters contains, among others, dissolved minerals and trace elements. These waters are known to be employed for the purpose of specific treatment according to the trace elements and the particular minerals which they contain, such as the hydration and desensitization of the skin or the treatment of some types of dermatitis. Mineral or thermal waters will denote not only natural mineral or thermal waters, but also natural mineral or thermal waters enriched in additional mineral constituents and/or trace elements, as well as aqueous mineral and/or trace-element solutions prepared from purified water (demineralized or distilled).

A natural thermal or mineral water employed according to the invention may, for example, be chosen from among Vittel water, Vichy bassin waters, Uriage water, Roche Posay water, Bourboule water, Enghien-les-Bains water, Saint Gervais-les-Bains water, Néris-les-Bains water, Allevard-les-Bains water, Digne water, Maizières water, Neyrac-les-Bains water, Lons-le-Saunier water, les Eaux Bonnes water, Rochefort water, Saint Christau water, Fumades water and Tercis-les-bains water, Uriage-les-bains water and Avene water.

The cosmetic compositions of the invention may additionally contain water-soluble or liposoluble adjuvants which are usual in the field of cosmetics, such as preserving agents, antioxidants, perfumes, screening agents, colorants, pearlescent agents and hydrophilic or lipophilic active substances.

They may also contain insoluble fillers: examples include polyethylene powder, polyamide particles like, for example, those sold under the name "Orgasol" by Atochem, also known under the names (CTFA) of "polyamide 12" or "polyamide 6". It is also possible to employ in these compositions kaolin and nylon powders listed under the CTFA name of "Nylon 12" or "Nylon 6". Such compositions are advantageous in skin cleaning owing to their exfoliating properties.

The compositions according to the invention have the appearance of a stable, transparent gel. In addition, these compositions have a very good rinsability. In particular, the $C_5$–$C_7$ carbohydrate fatty esters give these compositions a rinsability which is improved in relation to the compositions based on sucrose esters and those based on sorbitol esters.

Other subject-matter of the invention is the use of $C_5$–$C_7$ carbohydrate fatty esters in a composition including:

(i) a fatty phase, and (iii) at least one polyol, to improve the rinsability of this composition, and methods of cleansing the face and/or body by washing with invention compositions.

The compositions according to the invention can be presented, for example, in the form of a cleaning product, make-up remover, of a hydrating product, of a deep-cleanser, an exfoliating agent, etc.

EXAMPLES

In each composition the percentages are given as weight of material in relation to the total weight of the composition.

The viscosity is measured at 25° C. with a Rheomat 180 viscometer and the viscosity measurements are given in Pascal seconds (Pa s).

Body and Face Cleaning Composition

| Aqueous phase: | |
|---|---|
| Oxyethylenated methylglucose sesquistearate (20 EO) | 5% |
| Glycerol | 11% |
| Water | 5% |
| Oily phase: | |
| Liquid petrolatum | 10% |
| 2-Ethylhexyl palmitate | 15% |
| Hydrogenated isoparaffin | 9% |
| Cyclopentadimethylsiloxane | 9% |
| Isododecane | 25% |
| Perfume | q.s. |
| Preserving agent | q.s. |

Procedure: the glucose derivative is dissolved in water and the polyols with stirring between 25° C. and 35° C. until a homogeneous viscous paste is obtained. The oily phase is then introduced slowly with vigorous stirring. The product is then smoothed with the blade and freed from bubbles under vacuum.

This composition has a clear, transparent, gelled appearance and a Rheomat viscosity of 9.0 Pa s. This product, which is employed under the shower, allows a gentle effective cleaning. It leaves the skin smooth and clean without residue or oily film.

Composition for Removing Make-up

| Aqueous phase | |
|---|---|
| Oxyethylenated methylglucose sesquistearate (20 EO) | 1% |
| Oxyethylenated methylglucose dioleate (120 EO) | 3% |
| Glycerol | 15% |
| Water | 4% |
| Oily phase: | |
| Liquid petrolatum | 10% |
| 2-Ethylhexyl palmitate | 25.5% |
| Hydrogenated isoparaffin | 9% |
| Cyclopentadimethylsiloxane | 14% |
| Isododecane | 18.5% |
| Perfume | q.s. |
| Preserving agent | q.s. |

This composition has a clear, transparent gelled appearance and a Rheomat viscosity equal to 7.3 Pa s. The spreading of the product on the skin is easy and the rinsability excellent. After rinsing the skin is clean and feels silky, not greasy.

Exfoliating Composition

| A) Aqueous phase | |
|---|---|
| Oxyethylenated methylglucose sesquistearate (20 EO) marketed under the name Glucamate SSE 20 by Amerchol | 6% |
| Glycerol | 8% |
| Lactic acid | 1% |
| Water | 7% |
| B) Oily phase | |
| Isononyl isononanoate | 15% |
| Hydrogenated isoparaffin | 9% |
| Cyclopentadimethylsiloxane | 19% |
| Tetramethylhexane-heptane-octane | 30% |
| Perfume | q.s. |
| Preserving agent | q.s. |
| C) Polyethylene powder | 5% |

This exfoliating gel composition for rinsing with water gives a skin which is perfectly cleaned and smooth and uniform in appearance. It has a Rheomat viscosity equal to 9.0 Pa s.

COMPARATIVE TESTS

To show the advantage of the compositions according to the invention in relation to the compositions of the prior art the following tests were carried out:

Compositions 1a, 1b, 1c (according to the invention)

| Aqueous phase: | | | |
|---|---|---|---|
| Oxyethylenated methylglucose sesquistearate (20 EO) | 4.6% | | |
| Glycerol | 11% | | |
| Water | 5.9% | | |
| Oily phase: | 78.5% | | |
| alternative forms of the oily phase: | | | |
| Composition | 1a | 1b | 1c |
| liquid petrolatum | 10% | 12% | 0% |
| 2-ethylhexyl palmitate | 15% | 0% | 25.5% |
| hydrogenated isoparaffin | 9% | 22% | 12.5% |
| cyclopentadimethylsiloxane | 14% | 10% | 15.2% |
| $C_{11}$–$C_{30}$ isoparaffin | 30.5% | 0% | 25.3% |
| isododecane | 0% | 34.5% | 0% |

Procedure: same as above.

| Compositions | 2a | 2b | 2c (according to the prior art): |
|---|---|---|---|
| Aqueous phase for 2a, 2b and 2c: | | | |
| Oxyethylenated sorbitan monostearate (20 EO) | | | 4.6% |
| Glycerol | | | 11% |
| Water | | | 5.9% |
| Oily phase: | | | 78.5% |
| (same alternative forms as 1a, 1b, 1c above for the oily phase of 2a, 2b, 2c respectively) | | | |

Procedure: same as above.

Composition 3c (according to the prior art)

| Aqueous phase: | |
|---|---|
| Sucrose palmitostearate | 4.6% |
| Glycerol | 11% |
| Water | 78.5% |

(the same as for composition 1c)
Procedure: same as above.

The rinsability of the compositions according to the invention and according to the prior art was evaluated. Rinsability is intended to mean the ability of the composition to be removed rapidly after contact with water. The following test was employed to evaluate the rinsability of the various compositions:

0.5 ml of the transparent gelled composition are deposited onto 15 ml of water contained in a flask. The development of turbidity following the dispersion of the gel in water is measured. The faster the turbidity increases as a function of time, the faster the dispersion of the gel in water and hence the better the rinsability.

FIGS. I, II and III each show the development of turbidity of two aqueous solutions on which 0.5 ml of rinsable gel are deposited (Compositions 1a and 2a, 1b and 2b, 1c, 2c and 3c respectively).

Whatever the composition of the oily phase, a very clear superiority of the compositions including carbohydrate esters according to the invention, in relation to those including sorbitol esters, is found in the rinsability test.

The rinsability of the compositions including carbohydrate ester;, according to the invention is overall greatly superior to those including sucrose palmitostearate. In addition, formulation 3c, including sucrose palmitostearate, presents a stability problem: oil separation is observed on storage. This formulation also has the disadvantage of leaving a greasy film on the skin after rinsing.

Compositions according to the invention preferably have the appearance of, or include, a transparent gel.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A cosmetic composition consisting essentially of:
   (i) a fatty phase,
   (ii) at least one fatty acid ester of a $C_5$–$C_7$ carbohydrate, and
   (iii) at least one polyol.

2. The cosmetic composition according to claim 1, wherein the $C_5$–$C_7$ carbohydrate is selected from the group consisting of pentoses, hexoses and heptoses and their $C_{1-6}$ alkyl holoside derivatives.

3. The cosmetic composition according to claim 1, wherein the $C_5$–$C_7$ carbohydrate fatty holoside is 1-methylglucoside.

4. The cosmetic composition according to claim 1, wherein the fatty acid ester of a $C_5$–$C_7$ carbohydrate is a compound obtained by reaction of a fatty acid containing a saturated or unsaturated chain containing from 8 to 30 carbon atoms with a $C_5$–$C_7$ carbohydrate.

5. The cosmetic composition according to claim 1, wherein said fatty acid of a $C_5$–$C_7$ carbohydrate is oxyalkylenated.

6. The cosmetic composition according to claim 1, wherein the fatty acid ester of a $C_5$–$C_7$ carbohydrate is etherified by one or more oxyethylene or oxypropylene fragments, the total of the oxyethylene or oxypropylene substituents representing from 5 to 200 alkylene oxide units.

7. The cosmetic composition according to claim 1, wherein the fatty ester of a carbohydrate is a compound of formula (I):

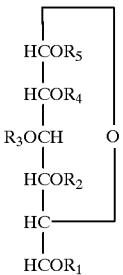

in which
$R_1$ is a group of formula (III):

wherein R' is selected from the group consisting of $C_8$–$C_{30}$ saturated or unsaturated, linear or branched alkyl groups; $R_2$, $R_3$ and $R_4$, which are identical or different, denote a group selected from the group consisting of a hydrogen atom, a group of formula (II): —$(C_nH_{2n}O)_p$—R (II), wherein n=2 or 3, p is an integer ranging from 2 to 50, R denotes a hydrogen atom or a $C_1$–$C_6$ alkyl group; a group of formula (III):

—OC—R' (III), wherein R' is selected from the group consisting of $C_8$–$C_{30}$ saturated or unsaturated, linear or branched alkyl groups; at least one of $R_2$, $R_3$ and $R_4$ being a group of formula (II), the total of the oxyalkylene residues, $\Sigma p$, ranging from 5 to 200; and $R_5$ is a saturated or unsaturated, linear or branched, $C_1$–$C_6$ alkyl group.

8. The cosmetic composition according to claim 7, wherein $R_5$=$CH_3$, wherein at least two groups of $R_2$, $R_3$ and $R_4$ correspond to formula (II), $\Sigma p$ is 15 to 150, R=H, at least one group of $R_1$, $R_2$, $R_3$ and $R_4$ corresponds to formula (III), R' is selected from the group consisting of $C_{16}$–$C_{20}$, alkyl groups, and none of the groups $R_2$, $R_3$ and $R_4$ is a hydrogen atom.

9. The composition according to claim 1, consisting of by weight relative to the total weight of the composition, from 0.5 to 50% of a fatty acid ester of a $C_5$–$C_7$ carbohydrate.

10. The composition according to claim 1, wherein the polyol is selected from the group consisting of ethylene glycol, propylene glycol, 1,3-butylene glycol, dipropylene glycol, glycerin, diglycerin, triglycerin, tetraglycerin, glucose, maltose, maltitol, sucrose, fructose, sorbitol, sugars originating from the decomposition of starch and mixtures thereof.

11. The composition according to claim 1, consisting of 0.5 to 60% by weight relative to the total weight of the composition, of polyol.

12. The composition according to claim 1, wherein the fatty phase includes an oil or a mixture of oils which has a refractive index $n^0 \leq 1.45$.

13. The composition according to claim 1, wherein the fatty phase represents from 1 to 95% by weight of the total weight of the composition.

14. The composition according to claim 1, wherein said composition is in the form of a cleaning product, make-up remover, of a hydrating product, of a deep-cleanser or of an exfoliating agent.

15. A cosmetic composition consisting essentially of:
   (i) a fatty phase,
   (ii) at least one fatty acid ester of a $C_5$–$C_7$ carbohydrate,
   (iii) at least one polyol, and
   (iv) water.

16. The cosmetic composition according to claim 15, wherein said water is present in an amount of 0.01 to 30% by weight.

17. The cosmetic composition according to claim 15, wherein said water is a mineral or spring water.

18. A cosmetic composition consisting essentially of:
   (i) a fatty phase,
   (ii) at least one fatty acid ester of a $C_5$–$C_7$ carbohydrate,
   (iii) at least one polyol, and
   (iv) at least one insoluble filler selected from the group consisting of kaolin, polyethylene powder, polyamide particles and nylon powder.

19. A process of forming an improved rinsability composition comprising adding a fatty acid ester of a $C_5$–$C_7$ carbohydrate to a composition comprising:
   (i) a fatty phase, and
   (iii) at least one polyol.

20. A method of cleansing the face and/or body, comprising washing said face and/or body with the composition of claim 1.

* * * * *